US012780870B2

(12) United States Patent
Wayal et al.

(10) Patent No.: US 12,780,870 B2
(45) Date of Patent: Nov. 3, 2026

(54) SMALL-MOLECULE PEPTIDE AND USE THEREOF AGAINST METABOLIC-ASSOCIATED FATTY LIVER DISEASE AND FOR REDUCING BODY WEIGHT

(71) Applicant: Tunghai University, Taichung City (TW)

(72) Inventors: Vipul Wayal, Tal-Ambegoan (IN); Chang-Chi Hsieh, Taichung (TW)

(73) Assignee: Tunghai University, Taichung City (TW)

( * ) Notice: Subject to any disclaimer, the term of this patent is extended or adjusted under 35 U.S.C. 154(b) by 531 days.

(21) Appl. No.: 18/462,852

(22) Filed: Sep. 7, 2023

(65) Prior Publication Data

US 2024/0409581 A1 Dec. 12, 2024

(30) Foreign Application Priority Data

Jun. 8, 2023 (TW) ................................ 112121475

(51) Int. Cl.

| | |
|---|---|
| ***C07K 5/065*** | (2006.01) |
| ***A61P 1/16*** | (2006.01) |
| ***A61P 3/04*** | (2006.01) |
| ***A61P 3/06*** | (2006.01) |
| ***A61P 3/10*** | (2006.01) |
| *A61K 38/00* | (2006.01) |

(52) U.S. Cl.

CPC ............ *C07K 5/06078* (2013.01); *A61P 1/16* (2018.01); *A61P 3/04* (2018.01); *A61P 3/06* (2018.01); *A61P 3/10* (2018.01); *A61K 38/00* (2013.01)

(58) Field of Classification Search

CPC .......... C07K 5/06078; A61P 1/16; A61P 3/04; A61P 3/06; A61P 3/10; A61K 38/00

See application file for complete search history.

(56) References Cited

FOREIGN PATENT DOCUMENTS

| | | | | | |
|---|---|---|---|---|---|
| CN | 105085631 | A | * | 11/2015 | |
| CN | 112795613 | A | * | 5/2021 | C07K 1/145 |
| JP | 6713981 | B2 | * | 6/2020 | A61K 38/00 |
| WO | WO2003004604 | A2 | * | 1/2003 | C40B 40/02 |

OTHER PUBLICATIONS

Joslin Education Team. (2020). Can Type 2 Diabetes Be Reversed? Joslin Diabetes Center. https://joslin.org/news-stories/all-news-stories/education/2020/03/can-type-2-diabetes-be-reversed (Year: 2020).*

Boulder Medical Team. (Sep. 13, 2015). Oral Hypoglycemic Drugs—Boulder Medical Center. Boulder Medical Center. https://www.bouldermedicalcenter.com/oral-hypoglycemic-drugs/ (Year: 2015).*

Wang, Y., Liu, Y., Gao, B., Yan, J., Cai, W., & Jiang, L. (2022). Untargeted Metabolomics Reveal Parenteral Nutrition-Associated Alterations in Pediatric Patients with Short Bowel Syndrome. Metabolites, 12(7), 600. https://doi.org/10.3390/metabo 12070600 (Year: 2022).*

Nanna, M., Peterson, E., & Navar, A. M. (Nov. 19, 2019). Hyperlipidemia not Associated with Cardiovascular Risk in Older Adults. Duke Health Referring Physicians. https://physicians.dukehealth.org/articles/hyperlipidemia-not-associated-cardiovascular-risk-older-adults (Year: 2019).*

Shahraz, J., Joukar, F., Sheida, F., Yeganeh, S., Maroufizadeh, S., Baghaee, M., Naghipour, M., & Mansour-Ghanaei, F. (2025). Associations Between Body Mass Index (BMI) and Dyslipidemia: Obesity science & practice, 11(1), e70055. https://doi.org/10.1002/osp4.700 (Year: 2025).*

Cambridge Dictionary. (2022). treating. @CambridgeWords. https://dictionary.cambridge.org/us/dictionary/english/treating#google_vignette (Year: 2022).*

World heart federation. (2023). CVD Prevention. World Heart Federation. https://world-heart-federation.org/what-we-do/prevention/ (Year: 2023).*

What medicine should be taken for fatty liver? (Jan. 25, 2025). Vinmec. https://www.vinmec.com/eng/blog/what-drugs-do-you-take-for-fatty-liver-en (Year: 2025).*

Chong Chen et al., Beyond antioxidant actions: Insights into the antioxidant activities of tyr-containing dipeptides in aqueous solution systems and liposomal systems, International Journal of Food Science & Technology, 2020, vol. 55, No. 10, 3227-3234.

Yi-Chieh Li et al., Lactoferrin dampens high-fructose corn syrup-induced hepatic manifestations of the metabolic syndrome in a murine model, PLoS One . May 9, 2014;9(5): e97341.

* cited by examiner

*Primary Examiner* — Lianko G Garyu
*Assistant Examiner* — Sachi Jauhari
(74) *Attorney, Agent, or Firm* — MUNCY, GEISSLER, OLDS & LOWE, P.C.

(57) ABSTRACT

A novel small-molecule peptide and a use thereof against metabolic-associated fatty liver disease (MAFLD) are disclosed. The small-molecule peptide has a sequence including Tyr and Phe. The small-molecule peptide has activity in inhibiting fat build-up in the liver, regulating metabolizing enzymes in the liver, and regulating the blood glucose level. The small-molecule peptide can be used to treat or improve MAFLD and MAFLD-related diseases.

2 Claims, 4 Drawing Sheets

Specification includes a Sequence Listing.

SMALL-MOLECULE PEPTIDE AND USE THEREOF AGAINST METABOLIC-ASSOCIATED FATTY LIVER DISEASE AND FOR REDUCING BODY WEIGHT

REFERENCE TO AN ELECTRONIC SEQUENCE LISTING

The content of the electronic sequence listing (2023-09-01 Sequence List.xml; Size: (2,867 bytes; and Date of Creation: Sep. 1, 2023) is herein incorporated by reference in its entirety.

BACKGROUND OF THE INVENTION

1. Technical Field

The present invention relates to a peptide and a use thereof. More particularly, the invention relates to a novel small-molecule peptide and a use thereof against metabolic-associated fatty liver disease and for reducing the body weight.

2. Description of Related Art

The liver is a major metabolic organ. Damage of liver cells will affect the metabolic function of the liver and result in various metabolic diseases, such as chronic hepatitis, cirrhosis, and hepatitis. Metabolic-associated fatty liver disease (hereinafter referred to as MAFLD), also referred to as non-alcoholic fatty liver, is a metabolic disease of the liver that is caused by excessive build-up of fat in the liver. Excessive fat build-up in the liver may lead to lipotoxicity and such disorders as ballooning of liver cells and lobular inflammation. Patients with MAFLD are also subject to other metabolic diseases like obesity, hyperlipidemia, diabetes, and hypertension.

While the morbidity rate of MAFLD is rising, there is currently no clinical method that can treat MAFLD effectively: improvement of the symptoms of fatty liver depends entirely on a patient doing more exercise, going on a diet, and losing weight. However, as most patients have problem changing their lifestyles persistently, it has been a clinically important issue to develop methods for treating or improving MAFLD.

BRIEF SUMMARY OF THE INVENTION

The primary objective of the present invention is to provide a novel small-molecule peptide and a use thereof against MAFLD and for reducing the body weight. That is to say, the primary objective is to provide a small-molecule peptide that has activity in inhibiting the build-up of fat and regulating the metabolism of blood glucose so that by administering an effective amount of the small-molecule peptide, diseases caused by metabolic imbalance, in particular fatty liver and diseases related thereto, can be treated or prevented effectively.

To achieve the foregoing objective, the present invention discloses a small-molecule peptide whose amino acid sequence includes a sequence of Tyr-Phe or Phe-Tyr.

More specifically, the amino acid sequence of the small-molecule peptide disclosed herein includes the sequence of SEQ ID No.: 1 or SEQ ID No.: 2.

In one embodiment of the present invention, the small-molecule peptide is a dipeptide whose amino acid sequence is Tyr-Phe or Phe-Tyr.

In another embodiment of the present invention, the small-molecule peptide is a tetrapeptide whose amino acid sequence is SEQ ID No.: 1 or SEQ ID No.: 2.

The small-molecule peptide disclosed herein has activity in inhibiting the build-up of fat and regulating the blood glucose level. Therefore, one embodiment of the present invention discloses a method for treating and/or preventing metabolic-associated fatty liver disease (MAFLD) and MAFLD-related disorders or reducing the body weight, blood sugar or lipid content by administrating a composition to a subject in need thereof, wherein the composition an effective amount of any one, or a combination, of the foregoing small-molecule peptides.

The aforesaid MAFLD-related disorders may be associated with imbalance in blood glucose regulation. Some notable examples of such MAFLD-related disorders are diabetes, hyperglycemia, and insulin dysfunction.

The aforesaid MAFLD-related disorders may be associated with fat build-up or imbalance in the metabolism of fat. Some notable examples of such MAFLD-related disorders are hypertension, hyperlipidemia, cardiovascular diseases, and obesity.

Another embodiment of the present invention discloses a composition that can be a food, nutrition supplement, pharmaceutical, or functional food.

DETAILED DESCRIPTION OF THE INVENTION

Figure 1:
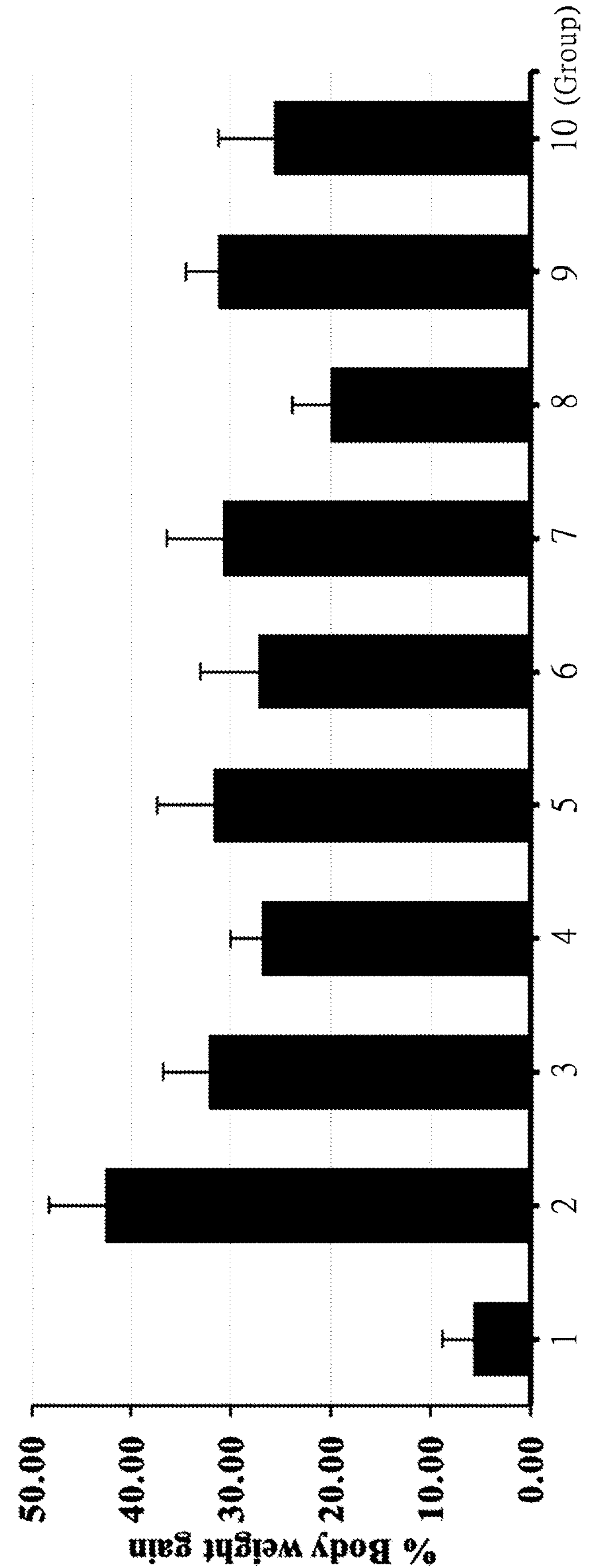
FIG. 1 is a bar chart showing the percent body weight gains of different groups of mice.

The present invention provides a novel small-molecule peptide and a use thereof against MAFLD and for reducing the body weight. The small-molecule peptide includes a sequence having at least two amino acids of Tyr and Phe. More specifically, the small-molecule peptide essentially includes one of the following amino acid sequences: Tyr-Phe (YF); Phe-Tyr (FY): SEQ ID No.: 1 (EWYF); and SEQ ID No.: 2 (EWFY). The small-molecule peptide disclosed herein has activity in inhibiting the build-up of fat in the liver, regulating metabolizing enzymes in the liver, and regulating the blood glucose level. Therefore, the small-molecule peptide disclosed herein can be used to treat or improve MAFLD and MAFLD-related diseases or reduce the body metabolism index, such as body weight, fasting blood sugar, lipid content. In other words, the small-molecule peptide disclosed herein can serve as an active ingredient of a composition for treating or improving MAFLD and MAFLD-related diseases or reducing the body weight, blood sugar or lipid content.

The aforesaid MAFLD-related diseases include hyperlipidemia, diabetes, hyperglycemia, obesity, cardiovascular diseases, the lipid metabolism imbalance syndrome, and so on.

In one embodiment of the present invention, the small-molecule peptide consists of two amino acids and the amino acid sequence thereof is Tyr-Phe (YF) or Phe-Tyr (FY).

In another embodiment of the present invention, the small-molecule peptide consists of four amino acids and the amino acid sequence thereof is SEQ ID No.: 1 or SEQ ID No.: 2.

The small-molecule peptide disclosed herein can be obtained by an artificial synthesis method, a biosynthesis method, or other conventional peptide preparation methods in the field to which the present invention pertains, or by extraction from a natural product. The method by which the small-molecule peptide is obtained has no effect on the effect of the small-molecule peptide or the scope of the patent protection sought by the applicant.

The term "small-molecule peptide" refers to a molecule having a molecular weight less than 5000 Da. The small-molecule peptide disclosed herein is composed of two to four amino acids.

The term "composition" refers to a product (e.g., a pharmaceutical, nutrition supplement, or food) that includes an effective amount of the small-molecule peptide disclosed herein, wherein the effective amount can be adjusted according to the individual to which the product is administered. The composition may be in the dosage form of an injection drug, powder, tablet, capsule, or other commonly used dosage forms.

The term "effective amount" refers to a dose capable of achieving the intended effect on an individual. The effective amount may vary with such parameters as the method of use, the method of administration, and the product type. Generally speaking, the effective amount of the small-molecule peptide disclosed herein in a composition is 0.01%-100% of the total weight of the composition.

The term "extraction" refers to a procedure of separating a target substance from a mixture. For example, the target substance is separated from the mixture by taking advantage of the difference in solubility of each substance in different solvents. The term may also include concentration, purification, and other procedures that are performed after the extraction in order to increase the purity of the target substance.

The term "artificial synthesis method" refers to a method for synthesizing a peptide by connecting a plurality of amino acids with a peptide chain.

The term "biosynthesis method" refers to a method by which: a nucleotide sequence capable of expressing a target peptide is introduced into a host by a genetic engineering method, the host is cultured in order to obtain a metabolite containing the target peptide, and the target peptide is obtained by such procedures as separation and purification.

The technical features and effects of the present invention are detailed below with reference to some experimental examples in conjunction with the accompanying drawings.

The amino acid sequences of the four peptides used in the following examples are: Tyr-Phe (YF): Phe-Tyr (FY); the sequence of SEQ ID No.: 1; and the sequence of SEQ ID No.: 2. All the peptides were artificially synthesized, and their amino acid compositions were verified.

The doses used in the following examples were calculated for, and based on, the test animals. Those doses were not intended to limit the scope of the present invention. In other words, a person of ordinary skill in the art may adjust the dose of each peptide according to the individual to which the peptide is administered and the dosage form of the peptide as well as general common knowledge.

Example 1: Animal Test 100 five-week-old C57BL/6JNarl mice (male) were raised in an environment whose temperature was 22-25° C., whose relative humidity was 45%-60%, and which adopted a 12-hour light/12-hour darkness cycle. The mice were fed with common feed and water for three weeks and then randomly divided into 10 groups, whose subsequent treatments are as follows:

Group 1: This was the blank group. The mice in this group were fed with common animal feed and distilled water.

Group 2: This was the control group. The mice in this group were fed with a diet with 60% kcal fat+30% v/v fructose corn syrup (and a 0.5% carboxymethyl cellulose (CMC) solution) and thereby induced to develop into MAFLD-mode mice.

Group 3: This was the low-dosage YF dipeptide group. The mice in this group were fed with the Tyr-Phe dipeptide at a dose of 10 mg/kg/day, in addition to a diet with 60% kcal fat+30% v/v fructose corn syrup.

Group 4: This was the high-dosage YF dipeptide group. The mice in this group were fed with the Tyr-Phe dipeptide at a dose of 50 mg/kg/day, in addition to a diet with 60% kcal fat+30% v/v fructose corn syrup.

Group 5: This was the low-dosage FY dipeptide group. The mice in this group were fed with the Phe-Tyr dipeptide at a dose of 10 mg/kg/day, in addition to a diet with 60% kcal fat+30% v/v fructose corn syrup.

Group 6: This was the high-dosage FY dipeptide group. The mice in this group were fed with the Phe-Tyr dipeptide at a dose of 50 mg/kg/day, in addition to a diet with 60% kcal fat+30% v/v fructose corn syrup.

Group 7: This was the low-dosage EWYF tetrapeptide group. The mice in this group were fed with the Glu-Trp-Tyr-Phe tetrapeptide (which has the sequence of SEQ ID No.: 1) at a dose of 10 mg/kg/day, in addition to a diet with 60% kcal fat+30% v/v fructose corn syrup.

Group 8: This was the high-dosage EWYF tetrapeptide group. The mice in this group were fed with the Glu-Trp-Tyr-Phe tetrapeptide (which has the sequence of SEQ ID No.: 1) at a dose of 50 mg/kg/day, in addition to a diet with 60% kcal fat+30% v/v fructose corn syrup.

Group 9: This was the low-dosage EWFY tetrapeptide group. The mice in this group were fed with the Glu-Trp-Phe-Tyr tetrapeptide (which has the sequence of SEQ ID No.: 2) at a dose of 10 mg/kg/day, in addition to a diet with 60% kcal fat+30% v/v fructose corn syrup.

Group 10: This was the high-dosage EWFY tetrapeptide group. The mice in this group were fed with the Glu-Trp-Phe-Tyr tetrapeptide (which has the sequence of SEQ ID No.: 2) at a dose of 50 mg/kg/day, in addition to a diet with 60% kcal fat+30% v/v fructose corn syrup.

Each of the four peptides was mixed with 0.5% Carboxymethyl Cellulose (CMC) to form a peptide solution, before the peptide solution was fed into the stomach of each mouse in the corresponding group with a syringe.

The test lasted eight weeks. The body weights of, and the amounts of food consumed by, the mice in each group were measured and recorded each week. The mice were sacrificed at the end of the test, and the livers, spleens, and white adipose tissue of the mice in each group were weighed. The results are shown in Table 1, Table 2, and FIG. 1.

TABLE 1

| Body weights, liver weights, and spleen weights of the mice in each group | | | | |
|---|---|---|---|---|
| Group | Initial body weight (g) | Final body weight (g) | Liver weight (g) | Spleen weight (mg) |
| 1 | 22.77 ± 1.07 | 24.05 ± 1.03 | 0.914 ± 0.068 | 41.8 ± 5.0 |
| 2 | 22.85 ± 1.29 | 32.59 ± 2.50 | 1.223 ± 0.107 | 68.7 ± 8.8 |
| 3 | 22.82 ± 1.01 | 30.22 ± 2.07 | 0.996 ± 0.094 | 59.9 ± 8.2 |
| 4 | 22.84 ± 1.25 | 28.98 ± 1.76 | 0.982 ± 0.085 | 53.8 ± 6.4 |
| 5 | 22.88 ± 1.09 | 30.10 ± 1.29 | 1.037 ± 0.089 | 58.8 ± 7.2 |
| 6 | 22.75 ± 1.10 | 28.93 ± 1.27 | 0.991 ± 0.078 | 54.2 ± 5.6 |
| 7 | 22.84 ± 1.71 | 29.76 ± 1.77 | 0.988 ± 0.084 | 55.5 ± 6.4 |

TABLE 1-continued

| Body weights, liver weights, and spleen weights of the mice in each group | | | | |
|---|---|---|---|---|
| Group | Initial body weight (g) | Final body weight (g) | Liver weight (g) | Spleen weight (mg) |
| 8 | 22.82 ± 1.13 | 27.42 ± 1.97 | 0.973 ± 0.089 | 51.2 ± 5.9 |
| 9 | 22.89 ± 1.08 | 30.04 ± 1.70 | 1.028 ± 0.068 | 56.6 ± 7.0 |
| 10 | 22.78 ± 1.79 | 28.59 ± 1.82 | 0.985 ± 0.072 | 53.5 ± 5.7 |

TABLE 2

| Weights of the epididymal, mesenteric, and perirenal white adipose tissue of the mice in each group | | | |
|---|---|---|---|
| Group | Epididymal white adipose tissue (g) | Mesenteric white adipose tissue (g) | Perirenal white adipose tissue (g) |
| 1 | 0.292 ± 0.054 | 0.069 ± 0.017 | 0.056 ± 0.019 |
| 2 | 1.738 ± 0.460 | 0.379 ± 0.103 | 0.599 ± 0.087 |
| 3 | 1.452 ± 0.433 | 0.298 ± 0.088 | 0.526 ± 0.069 |
| 4 | 1.182 ± 0.265 | 0.251 ± 0.056 | 0.481 ± 0.080 |
| 5 | 1.328 ± 0.234 | 0.289 ± 0.055 | 0.544 ± 0.077 |
| 6 | 1.220 ± 0.301 | 0.257 ± 0.067 | 0.487 ± 0.098 |
| 7 | 1.146 ± 0.306 | 0.263 ± 0.070 | 0.499 ± 0.060 |
| 8 | 0.909 ± 0.269 | 0.199 ± 0.061 | 0.418 ± 0.104 |
| 9 | 1.294 ± 0.330 | 0.276 ± 0.081 | 0.513 ± 0.132 |
| 10 | 0.983 ± 0.231 | 0.234 ± 0.056 | 0.445 ± 0.077 |

It can be known from the results in FIG. 1, Table 1, and Table 2 that the body weights, liver weights, spleen weights, and white adipose tissue weights of the mice in group 2 are significantly higher than those of the mice in group 1. This indicates that MAFLD-mode mice were successfully established. The results also show that the body weights, liver weights, spleen weights, and white adipose tissue weights of the mice in each of groups 3 to 10 are significantly lower than those of the mice in group 2. This indicates that each of the peptides disclosed herein, be it low-dosage or high-dosage, was effective in inhibiting the increase of body weight, liver weight, and spleen weight attributable to a high-sugar and high-fat diet, and in inhibiting the build-up of adipose tissue.

Example 2: Biochemical Analysis of Blood

After the test of example 1, blood samples were taken from the mice in each group, and the serum alanine transaminase (sALT), serum triglyceride (sTG), serum total cholesterol (sTC), serum free fatty acid (sFFA), and serum very-low-density lipoprotein (sVLDL) levels of the blood samples were measured. The results are shown in Table 3.

TABLE 3

| sALT levels and other blood lipid indices of the sera of the mice in each group | | | | | |
|---|---|---|---|---|---|
| Group | sALT (IU/L) | sTG (mg/dL) | sTC (mg/dL) | sFFA (mEq/L) | sVLDL (mg/dL) |
| 1 | 12.5 ± 3.49 | 65.52 ± 19.87 | 76.26 ± 17.76 | 0.447 ± 0.171 | 13.10 ± 3.97 |
| 2 | 77.7 ± 18.89 | 122.49 ± 27.21 | 182.55 ± 25.45 | 1.364 ± 0.404 | 24.50 ± 5.44 |
| 3 | 44.4 ± 15.09 | 103.38 ± 22.62 | 155.01 ± 25.12 | 0.932 ± 0.336 | 20.68 ± 4.52 |
| 4 | 36.3 ± 15.97 | 95.19 ± 24.70 | 140.70 ± 22.66 | 0.813 ± 0.243 | 19.04 ± 4.94 |
| 5 | 53.1 ± 21.40 | 106.80 ± 23.45 | 158.43 ± 20.37 | 1.03 ± 0.338 | 21.36 ± 4.69 |
| 6 | 42.6 ± 17.60 | 97.80 ± 22.91 | 146.76 ± 19.73 | 0.905 ± 0.179 | 19.56 ± 4.58 |
| 7 | 39.3 ± 20.17 | 96.18 ± 21.42 | 139.71 ± 20.52 | 0.782 ± 0.309 | 19.24 ± 4.28 |
| 8 | 27.9 ± 14.00 | 81.84 ± 20.39 | 126.96 ± 24.59 | 0.692 ± 0.24 | 16.37 ± 4.08 |
| 9 | 45.6 ± 13.91 | 100.53 ± 20.83 | 147.45 ± 25.19 | 0.849 ± 0.235 | 20.11 ± 4.17 |
| 10 | 34.2 ± 16.20 | 91.47 ± 18.50 | 135.78 ± 23.48 | 0.757 ± 0.303 | 18.29 ± 3.70 |

It can be known from the results in Table 3 that the blood lipid indices of the sera of the mice in group 2 are significantly higher than those of the mice in group 1. This indicates that the mice in group 2 had metabolic hyperlipidemia. The results also show that the sALT levels and other blood lipid indices of the sera of the mice in each of groups 3 to 10 are significantly lower than those of the mice in group 2.

The foregoing results indicate that each of the peptides disclosed herein, be it low-dosage or high-dosage, had activity in lowering the lipid content of serum and inhibiting liver-related enzymes. Therefore, it can be inferred that administration of an effective amount of each peptide, or of a composition containing the peptide, to an individual will be able to effectively improve or prevent liver-related diseases, hyperlipidemia, and hyperlipidemia-related metabolic diseases (e.g., cardiovascular lesions) that are attributable to a high-sugar and high-fat diet.

Example 3: Blood Glucose Test

On the last day of the test of example 1, the mice in each group were fasted, and the high-fructose corn syrup was changed to distilled water. After fasting for 12 hours, a 5 μL blood sample was taken from the tail vein of the mice in each group, and the blood glucose levels of the blood samples were measured as the fasting blood glucose (FBG) levels, as shown in FIG. 2.

Figure 3:
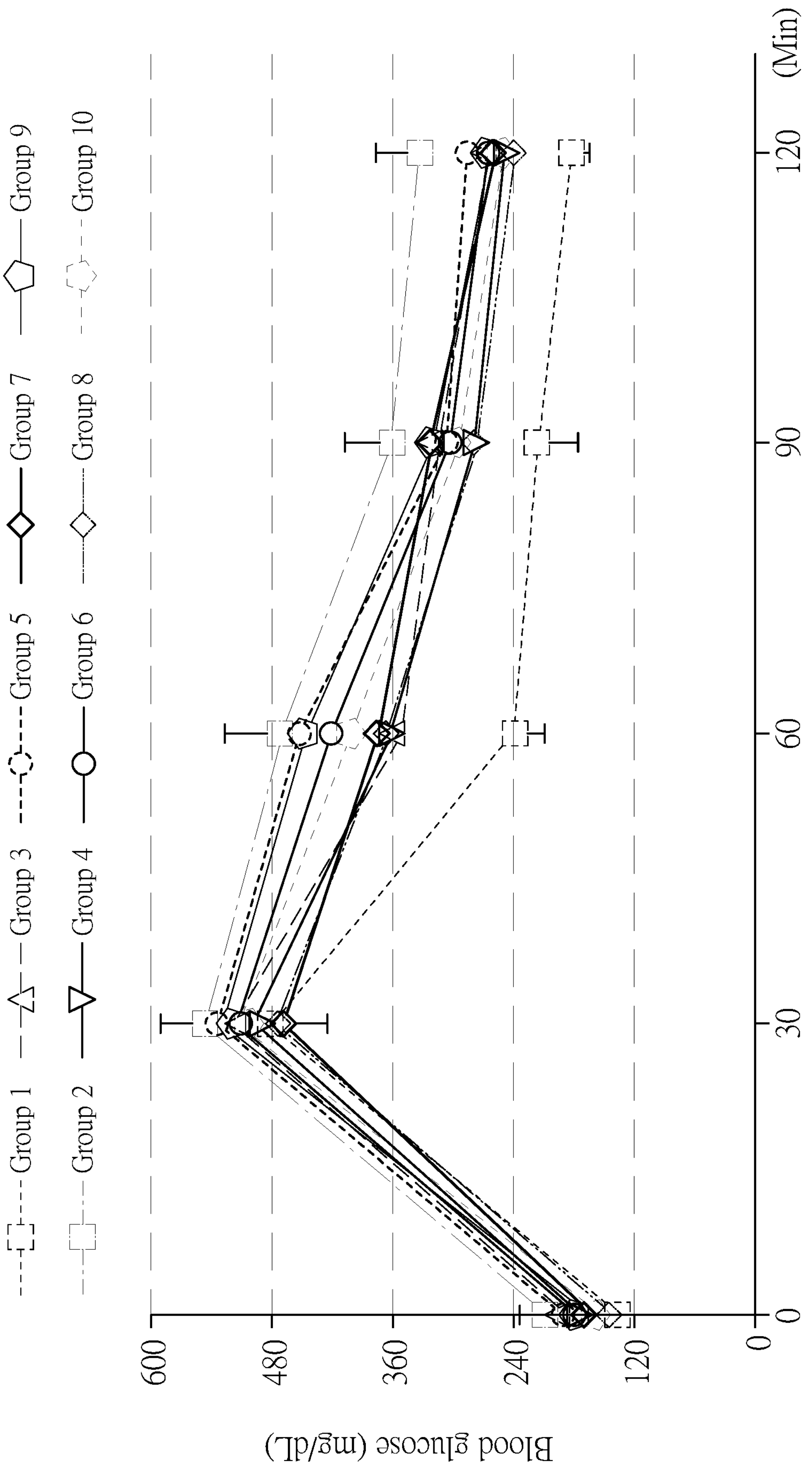
FIG. 3 is a plot showing the oral glucose tolerance test (OGTT) results of different groups of mice, or more particularly the blood glucose levels at the 0-minute, 30-minute, 60-minute, 90-minute, and 120-minute time points after the administration of glucose.
Figure 4:
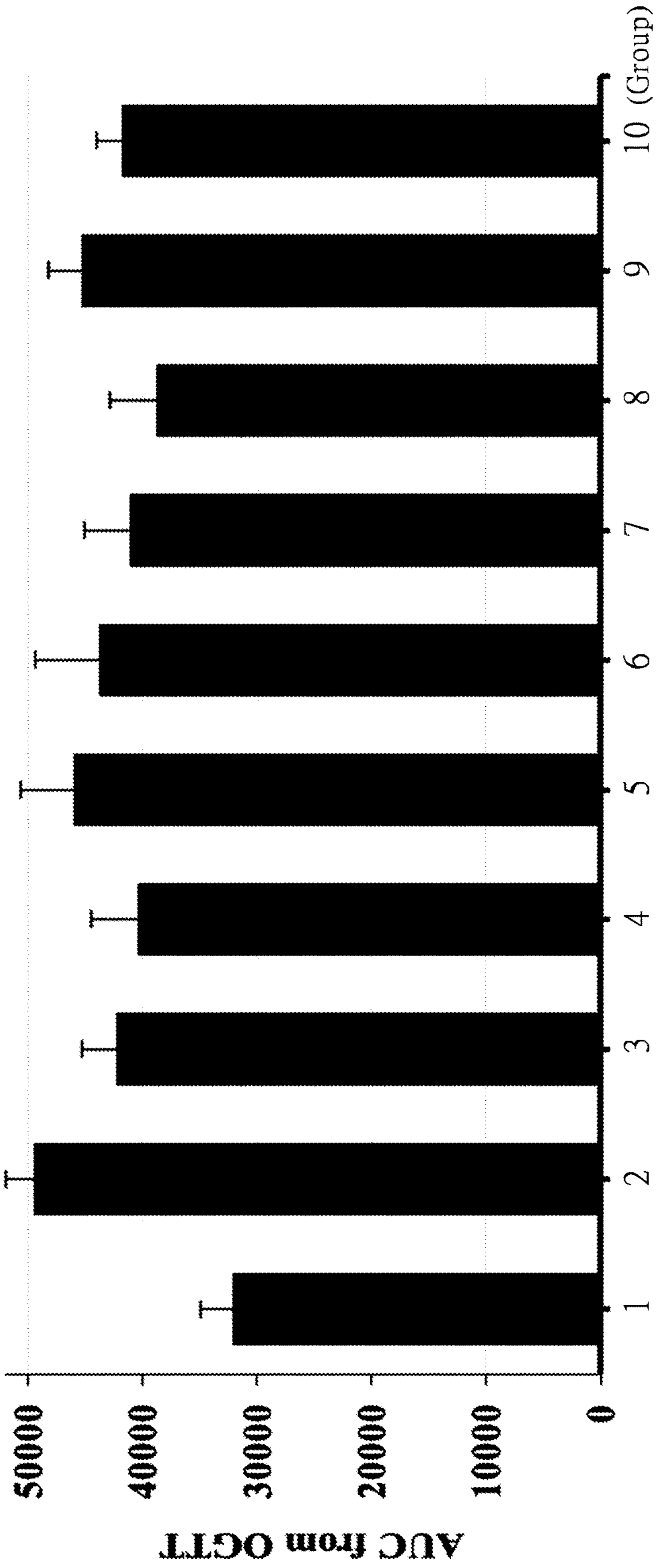
FIG. 4 is a bar chart showing the areas under curve (AUC) in FIG. 3.

The FBG levels were used as the 0-minute blood glucose levels in an oral glucose tolerance test (OGTT). D-glucose was subsequently administered into the stomach of each mouse at a dose of 2 g/kg body weight, and the blood glucose level of each mouse was measured at the 30-minute, 60-minute, 90-minute, and 120-minute time points after the administration of the glucose. FIG. 3 and FIG. 4 show the analysis results of the blood glucose measurements.

Figure 2:
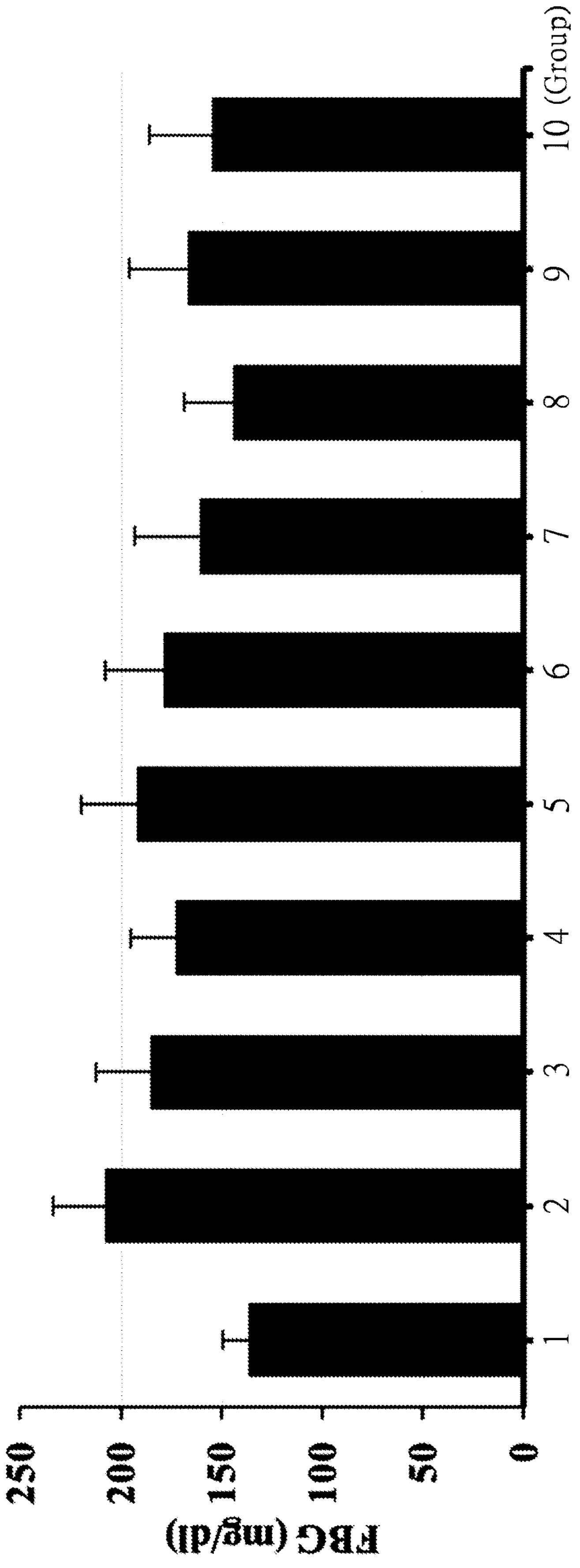
FIG. 2 is a bar chart showing the fasting blood glucose (FBG) levels of different groups of mice.

It can be known from the results in FIG. 2 to FIG. 4 that the FBG levels and the areas under the OGTT curve of the mice in each of groups 3 to 10 are significantly lower/smaller than those of the mice in group 2. This indicates that each of the peptides disclosed herein had activity in blood glucose regulation.

Therefore, it can be inferred that administration of an effective amount of each peptide, or a composition containing the peptide, to an individual on a high-fat and high-sugar diet will be able to stabilize the individual's blood glucose level and thereby prevent or treat diabetes or other diseases associated with imbalance in blood glucose.

Example 4: Analysis of the Hepatic Lipid Content

After the test of example 1, the mice in each group were sacrificed, and the livers of the mice were collected in order to measure the hepatic lipid content of the liver of each mouse by an enzymatic colorimetric method. The items measured were hepatic triglyceride (hTG), hepatic total cholesterol (hTC), hepatic free fatty acid (hFFA), and hepatic very-low-density lipoprotein (hVLDL), wherein the hVLDL level was calculated as ⅕ of the hepatic triglyceride level. Table 4 shows the analysis results of the measurements.

TABLE 4

Hepatic lipid contents of the mice in each group

| Group | hTG (mg/dL) | hTC (mg/dL) | hFFA (mEq/L) | hVLDL (mg/dL) |
|---|---|---|---|---|
| 1 | 22.47 ± 4.84 | 5.96 ± 0.91 | 74.05 ± 19.5 | 4.49 ± 0.97 |
| 2 | 52.78 ± 9.12 | 14.49 ± 1.42 | 139.45 ± 25.92 | 10.56 ± 1.82 |
| 3 | 41.81 ± 8.32 | 11.22 ± 1.23 | 110.93 ± 21.96 | 8.36 ± 1.66 |
| 4 | 36.95 ± 8.33 | 9.76 ± 1.45 | 98.90 ± 24.07 | 7.39 ± 1.67 |
| 5 | 44.58 ± 6.77 | 12.06 ± 1.19 | 119.27 ± 29.07 | 8.92 ± 1.35 |
| 6 | 41.49 ± 8.52 | 10.97 ± 1.2 | 112.49 ± 25.02 | 8.30 ± 1.70 |
| 7 | 39.45 ± 9.93 | 10.74 ± 1.38 | 108.17 ± 26.92 | 7.89 ± 1.99 |
| 8 | 31.49 ± 8.04 | 8.19 ± 1.07 | 87.71 ± 21.90 | 6.29 ± 1.61 |
| 9 | 41.45 ± 9.45 | 11.04 ± 1.11 | 111.78 ± 27.75 | 8.29 ± 1.89 |
| 10 | 22.47 ± 4.84 | 5.96 ± 0.91 | 74.05 ± 19.5 | 4.49 ± 0.97 |

It can be known from the results in Table 4 that the hTG, hTC, hFFA, and hVLDL levels of the livers of the mice in group 2 are significantly higher than those of the mice in group 1. This indicates that a high-fat and high-sugar diet did result in an increase in the hepatic lipid content, which in turn may lead to fatty liver or fatty liver-related metabolic diseases. The results also show that the hTG, hTC, hFFA, and hVLDL levels of the livers of the mice in each of groups 3 to 10 are significantly lower than those of the mice in group 2. This indicates that each of the peptides disclosed herein was effective in inhibiting the build-up of fat in the liver and reducing steatosis.

It can be inferred from the foregoing results that each of the peptides disclosed herein has activity in lowering the fat content of the liver. Therefore, administration of an effective amount of each peptide, or a composition containing the peptide, to an individual will be able to improve or prevent MAFLD or MAFLD-related disorders.

SEQUENCE LISTING

```
Sequence total quantity: 2
SEQ ID NO: 1          moltype = AA  length = 4
FEATURE               Location/Qualifiers
source                1..4
                      mol_type = protein
                      organism = synthetic construct
SEQUENCE: 1
EWYF                                                             4

SEQ ID NO: 2          moltype = AA  length = 4
FEATURE               Location/Qualifiers
source                1..4
                      mol_type = protein
                      organism = synthetic construct
SEQUENCE: 2
EWFY                                                             4
```

What is claimed is:

1. A method for improving metabolic-associated fatty liver disease (MAFLD), hyperlipidemia or hyperglycemia administering a composition to a subject in need thereof, wherein the composition includes a small-molecule peptide, wherein the sequence of the small-molecule peptide consists of SEQ ID NO: 1 or SEQ ID NO: 2.

2. A method for reducing the body weight, blood sugar or lipid content comprising administering a composition to a subject in need thereof, wherein the composition includes a small-molecule peptide, wherein the sequence of the small-molecule peptide consists of SEQ ID NO: 1 or SEQ ID NO: 2.

* * * * *